(12) United States Patent
Solomon (10) Patent No.: US 8,298,596 B2
(45) Date of Patent: Oct. 30, 2012

(54) LACTASE FORMULATION

(76) Inventor: Neil A. Solomon, San Francisco, CA (US)

( * ) Notice: Subject to any disclaimer, the term of this patent is extended or adjusted under 35 U.S.C. 154(b) by 0 days.

(21) Appl. No.: 12/031,541

(22) Filed: Feb. 14, 2008

(65) Prior Publication Data

US 2008/0193598 A1   Aug. 14, 2008

Related U.S. Application Data

(60) Provisional application No. 60/901,469, filed on Feb. 14, 2007.

(51) Int. Cl.
*A23C 9/12* (2006.01)
*A23C 9/00* (2006.01)

(52) U.S. Cl. ............ 426/61; 426/63; 426/587

(58) Field of Classification Search ............ 426/52, 426/63, 587, 61
See application file for complete search history.

(56) References Cited

U.S. PATENT DOCUMENTS

| | | | |
|---|---|---|---|
| 3,193,393 A | 7/1965 | Scott | |
| 3,718,739 A * | 2/1973 | Cayle | 424/94.61 |
| 4,464,469 A * | 8/1984 | Parr et al. | 435/188 |
| 5,302,400 A * | 4/1994 | Sipos | 424/494 |
| 5,885,618 A * | 3/1999 | Knap et al. | 424/499 |
| 5,902,617 A | 5/1999 | Pabst | |
| 5,955,096 A * | 9/1999 | Santos et al. | 424/434 |
| 6,008,027 A | 12/1999 | Langner | |
| 6,242,405 B1 | 6/2001 | Lykke et al. | |
| 6,344,196 B1 | 2/2002 | Kligerman | |
| 6,365,208 B1 | 4/2002 | Kulkarni et al. | |
| 6,428,786 B1 | 8/2002 | Eisenhardt et al. | |
| 6,562,338 B2 | 5/2003 | Eisenhardt et al. | |
| 6,562,339 B2 | 5/2003 | Eisenhardt et al. | |
| 6,660,302 B1 | 12/2003 | Gayser, Jr. | |
| 6,680,184 B2 | 1/2004 | Nussinovitch | |
| 6,808,557 B2 * | 10/2004 | Holbrey et al. | 426/650 |
| 6,989,169 B2 * | 1/2006 | Ripoll et al. | 426/235 |
| 7,204,997 B2 * | 4/2007 | Bromberg et al. | 424/487 |
| 2002/0187139 A1 * | 12/2002 | Eisenhardt et al. | 424/94.6 |
| 2003/0096040 A1 * | 5/2003 | Mehta et al. | 426/100 |

FOREIGN PATENT DOCUMENTS

EP   1208848   5/2002

OTHER PUBLICATIONS

NPL Cajori FA, "Intestinal Lactase": Cajori FA, "The lactase activity of the intestinal mucosa of the dog and some characteristics of intestinal lactase" J Biol Chem, 109 (1) : pp. 159-168, 1934.*
NPL: Metamucil Clear in food; http:// www.metamucil.com/clear-and-natural.php. , 1998 ( Date retrieved from Way back machine).*
International Search Report for PCT/US2008/054012, mailed Jun. 10, 2008, 10 pgs.
Lieberman et al., Pharmaceutical Dosage Forms: Tablets, vol. 3, pp. 114-116 (1990).

* cited by examiner

*Primary Examiner* — Humera Sheikh
*Assistant Examiner* — Bhaskar Mukhopadhyay
(74) *Attorney, Agent, or Firm* — McNeely Hare & War, LLP; William D. Hare (57) ABSTRACT

A particulate composition comprising a plurality of particles comprising lactase and a protective material are provided. The particles have a size that is not perceptible or is minimally perceptible on the human tongue. The particulate composition can be made by a method that comprises the steps of providing a lactase, providing a protective material, and forming a particulate composition comprising a plurality of particles comprising the lactase and the protective material in a size that is not perceptible or barely perceptible on the human tongue. The particulate composition can be used by applying the lactase composition to a food article or by using the lactase composition in the course of consuming the food article.

24 Claims, 2 Drawing Sheets

LACTASE FORMULATION

CROSS-REFERENCE TO RELATED APPLICATION

This application is a non-provisional application and claims the benefit of U.S. provisional application No. 60/901,469, filed on Feb. 14, 2007, the teaching of which is incorporated herein by reference in its entirety.

FIELD OF THE INVENTION

This invention generally relates to a lactase formulation and methods of making and using the same.

DESCRIPTION OF THE BACKGROUND

The human digestive system utilizes beta-galactosidase, more commonly known as lactase, to break down the complex sugar molecule lactose present in mammalian milks. Decreased lactase activity is common in many ethnic groups, usually appearing in childhood but with variable patterns of affliction. This condition causes symptoms of bloating, cramping, abdominal pain, and flatulence after ingestion of a dairy beverage or food, and this condition is known as lactose intolerance.

Lactose intolerance is currently treated in one of several ways. Many lactose intolerant individuals avoid dairy products. Because dairy is a major source of calcium, this is not a healthy behavior for many people. Milk that has been treated with lactase enzyme, thus hydrolyzing the lactose into glucose and galactose, is widely available commercially. Because glucose is a sweeter sugar than lactose, the resulting milk is thicker and sweeter than more traditional milk. A couple of other dairy products pre-treated to remove the lactose are also available, such as ice cream and cottage cheese. These products also have a different taste and consistency that the traditional lactose-containing diary counterparts.

A third method to treat lactose intolerance is to ingest lactase-containing tablets at the time the dairy is ingested. Such tablets are available at drug stores or on pharmaceutical aisles at groceries and other large retail stores. The open ingestion of pills conveys a medical problem, which can be awkward in public dining situations. Children may also find lactase tablets hard to ingest. Finally, the separation of the lactase from the site and time it is most needed makes it inconvenient and often unavailable.

A need therefore exists for a lactase enzyme food additive that does not change the texture and taste of the dairy. If lactase enzyme were embedded into food so as to act on the lactose after passing the taste buds it would not alter the desired taste of dairy products. If the lactase enzyme could be active in the stomach and small intestine it would also hydrolyze the lactose and prevent symptoms of lactose intolerance. By embedding the lactase enzyme into toppings, condiments and foods consumed with dairy this objective can be achieved.

The formulation and methods of making and using the same disclosed herein address the above-described issues and needs.

SUMMARY OF THE INVENTION

According to an aspect of the present invention, it is provided a composition comprising a plurality of particles comprising lactase and a protective material. The particles have a size that minimizes their perception on the human tongue. The particles can be microcapsules encapsulating lactase or particles having a coating of the protective material on the particles. In some embodiments, the particles can be particles of a matrix material (a binding material) having lactase dispersed therein.

The composition disclosed herein can have a lactase concentration ranging from above 0 wt % to below 100 wt %. For example, the composition can have a concentration from about 5 wt % to about 95 wt % by the total weight of the composition.

The protective material can be any material commonly used in the food and/or pharmaceutical industry. Some examples of such protective material can be amylose acetate phthalates, styrene-maleic acid copolymer, cellulose acetate succinate, cellulose acetate phthalate, polyvinyl acetate phthalate, hydroxypropylmethylcellulose phthalate, fatty acids, hydroxypropyl methylcellulose (HPMC), glycerol triacetate (triacetin), Marcoat, gum acacia, glycerin, fatty acid esters, glycerol esters, polyglycerol esters, paraffin waxes, carnauba wax, formalized gelatin, shellac wax, hydrogenated vegetable waxes, or combinations thereof.

According to another aspect of the present invention, it is provided a method of fabricating a lactase composition. The method comprises: providing a lactase, providing a protective material, and forming a particulate composition comprising lactase and a protective material having particles in a size that is minimally perceptible on the human tongue. In some embodiments, the act of forming a particulate composition comprises filtering the particulate composition to generate particles in a size that is not perceptible or is barely perceptible on the human tongue. In some embodiments, the act of forming a particulate composition comprises causing the protective material to encapsulate lactase to generate microcapsules encapsulating lactase. In some embodiments, the act of forming a particulate composition comprises coating a protective layer comprising the protective material on the particles. Embodiments of the particulate composition are as described above.

According to a further aspect of the present invention, it is provided a method of using a lactase composition as described herein. The method comprises: applying the lactase composition to a food article or using the lactase composition in the course of consuming the food article. The composition comprises a plurality of particles comprising lactase and a protective material, and the particles have a size that is not perceptible or is barely perceptible on the human tongue. Embodiments of the particulate composition are as described above. The food article can be any dairy product.

DETAILED DESCRIPTION OF THE INVENTION

According to one aspect of the present invention, it is provided a particulate composition comprising a plurality of particles comprising lactase and a protective material, the particles having a size that is not perceptible or is barely perceptible on the human tongue. The protective material stabilizes the lactase in a food article. The composition releases lactase in the course of digestion of the food article.

In some embodiments, the particles can be microcapsules encapsulating lactase or particles having a coating of the protective material on the particles. In some embodiments, the particle comprises a matrix material (a binding material) having lactase dispersed therein.

The composition disclosed herein can have a lactase concentration ranging from above 0 wt % to below 100 wt %. For example, the composition can have a lactase concentration from about 5 wt % to about 95 wt % by the total weight of the composition. In some embodiments, the particulate composition described herein can include lactase in concentrations such as about 10 wt %, about 20 wt %, about 30 wt %, about 40 wt %, about 50 wt %, about 60 wt %, about 70 wt %, about 80 wt %, or about 90 wt % of the total weight of the formulation.

In some embodiments, any of the forming steps described above can include filtering the particles formed above to generate particles having a certain size that is not perceptible or is barely perceptible on the human tongue.

In some embodiments, the particulate composition can be a solid formulation. For example, the particulate composition can be a powder or granules and can be put into shakers or packets to be sprinkles over dairy foods. The particulate composition can include conventional solid fillers or carriers, such as starch, talc, calcium phosphate, calcium sulfate, calcium stearate, magnesium stearate, stearic acid, sorbitol, mannitol, gelatin, natural or synthetic gums, such as carboxymethylcellulose, methylcellulose, alginates, dextrans, acacia gum, karaya gum, locust bean gum, tragacanth and other conventional carriers.

In some embodiments, the particulate composition can be a liquid formulation. For example, the particulate composition can be formulated into an aqueous or non-aqueous dispersion or suspension. Conventional liquid carriers such as glycerol, and edible glycols, edible oils, such as cottonseed oil, soybean oil, corn oil, peanut oil, safflower oil, and other triglyceride oils, and dispersing or suspending agents, such as the aforementioned natural and synthetic gums.

Conventional methods are employed for preparing the solid and liquid forms of the present invention. Suitable techniques are described in Remington's Pharmaceutical Sciences, 18th Ed., Chapters 83 and 89 (1990), which is hereby incorporated by reference.

The particulate composition described herein can be used in combination with any food article comprising a dairy product. Each serving includes an effective amount of lactase for lactose intolerance equivalent to about at least 9000 FCC lactase unit (FCC Lac U). Some exemplary amounts of lactase in each serving can be equivalent to about 10000 FCC Lac U, about 15000 FCC Lac U, about 20000 FCC Lac U, about 25000 FCC Lac U, about 30000 FCC Lac U, about 35000 FCC Lac U, about 40000 FCC Lac U, about 45000 FCC Lac U, or about 50000 FCC Lac U. In some embodiments, the amount of lactase in each serving can be equivalent to over 50000 FCC Lac U.

The particulate formulation described herein provides an effective solution to the problem of lactose intolerance. The composition disclosed herein makes lactase easier to utilize for dairy consumers. The formulation lactase is stable and can be applied to any food article that includes lactose. The formulation does not alter the taste of the food article. In addition, the formulation described herein allows lactase to be introduced into foods without changing the taste, smell or texture of the food.

Particle Sizes

The particulate composition includes particles having a size that is not perceptible or is barely perceptible on human tongue. Such particles generally have a size of 500 microns or below. In some embodiments, the particles have a size of about 400 microns or below, about 300 microns or below, about 200 microns or below, about 100 microns or below, about 50 microns or below, about 20 microns or below, about 10 microns or below, or about 1 micron or below. In some embodiments, the particles have a size of about 500 nanometers or below, about 200 nanometers or below, about 100 nanometers or below, about 50 nanometers or below, about 20 nanometers or below, or about 10 nanometers or below. Some exemplary ranges of size of the particles are from about 10 nm to about 500 μm, from about 100 nm to about 100 μm, from about 1μ to about 100 μm, or from about 10 μm to about 100 μm. Some exemplary microcapsules have a size of about 20 nm, about 50 nm, about 150 nm, about 200 nm, about 500 nm, about 750 nm, about 5 μm, about 15 μm, about 20 μm, about 30 μm, about 40 μm, about 50 μm, about 60 μM, about 70 μm, about 80 μm, about 90 μm, about 150 μm, about 200 μm, about 300 μm, or about 400 μm.

As used herein, the term "barely perceptible" can be used interexchangeably with the term "minimally perceptible."

The size of the particulate composition described herein is important to release of the lactase in the formulation. The size of the particles is positively related to the release rate of the lactase from the formulation. Generally, a particulate composition described herein having particles with a smaller size will have a faster release of lactase from the formulation, and a particulate composition described herein having particles with a larger size will have a slower release of lactase from the formulation. By varying the size of the particles in the particulate composition, different release profiles of lactase can be achieved such that one can tailor the size or size range of particles in a particulate composition described herein to meet different needs of lactase for addressing lactose intolerance.

Protective Materials

The protective material can be any material used in the food and pharmaceutical industry capable of stabilizing the lactase in a food article and allowing the lactase to be released in the course of digestion of the food article. In some embodiments, the protective material can be used for encapsulating, coating, or binding the lactase.

The protective material can comprise a natural material such as a natural polymer or a synthetic material such as a synthetic polymer. For example, in some embodiments, a protective material can be cellulose polymers and other ingredients listed as GRAS ("generally regarded as safe" with the FDA).

In some embodiments, the protective material is a coating material. Suitable coating materials for lactase include amylose acetate phthalates, styrene-maleic acid copolymer, cellulose acetate succinate, cellulose acetate phthalate, polyvinyl acetate phthalate, hydroxypropylmethylcellulose phthalate, fatty acids, hydroxypropyl methylcellulose (HPMC), glycerol triacetate (triacetin), Marcoat, gum acacia, glycerin, fatty acid esters, glycerol esters, polyglycerol esters, paraffin waxes, carnauba wax, formalized gelatin, shellac and hydrogenated vegetable waxes, such as hydrogenated castor oil and cottonseed oil. Other suitable coating materials are disclosed in Lieberman, H. A. et al., Pharmaceutical Dosage Forms: Tablets, Vol. 3, pp. 114-116 (1990), which is hereby incorporated by reference.

In some embodiments, the protective material is an encapsulating material such as lyposomes.

Methods of Preparation

According to another aspect of the present invention, it is provided a method of fabricating a lactase composition. The method comprises: providing a lactase, providing a protective material, and forming a particulate composition comprising lactase and a protective material having particles in a size that is not perceptible or barely perceptible on the human tongue. In some embodiments, the act of forming a particulate composition comprises filtering the particulate composition to generate particles in a size that is perceptible on the human tongue.

In some embodiments, the act of forming a particulate composition comprises causing the protective material to encapsulate lactase to generate microcapsules encapsulating lactase. In some embodiments, the act of forming a particulate composition comprises coating a protective layer comprising the protective material on the particles. In some embodiments, the act of forming a particulate composition comprises forming particles comprising a matrix material (a binding material) having lactase dispersed therein.

Embodiments of the particulate composition are as described above. Methods of forming microcapsules and methods of coating particles are described in more detail below.

A. Encapsulation

In some embodiments, the present invention provides a particulate composition of lactase that includes lactase encapsulated within microcapsules. Such encapsulated microcapsules can readily dissolve upon exposure to a physiological fluid, e.g., saliva, so as to release lactase encapsulated therein. In some embodiments, the microcapsules are stable in a neutral or slightly basic fluid but can be dissolved in an acidic environment to release lactase. In some embodiments, the microcapsules are stable in a neutral or slightly acidic fluid but can be dissolved in a basic environment to release lactase.

Materials forming the microcapsules can be any of the protective materials described above. Methods of encapsulating an enzyme or other active agents are documented. Some exemplary processes of encapsulation or microencapsulation of an enzyme are described at U.S. Pat. Nos. 5,902,617; 6,680,184 and 6,242,405.

B. Coating

In some embodiments, the formulation can comprise particles of lactase coated with a protective coating. The coating can readily dissolve upon exposure to a physiological fluid, e.g., saliva, so as to release lactase encapsulated therein. In some embodiments, the coating is stable in a neutral or slightly basic fluid but can be dissolved in an acidic environment to release lactase. In some embodiments, the coating is stable in a neutral or slightly acidic fluid but can be dissolved in a basic environment to release lactase.

Coatings can be formed on lactase particles by any known method. For example, a coating can be formed on the lactase particles by spray coating, or dipping. Materials forming the coating can be any of the protective materials described above.

Various methods for coating a particle is well established in the art (see, e.g., U.S. patent application publication No. 2004022938).

Food Articles

According to a further aspect of the present invention, it is provided a method of using a lactase composition as described herein. The method comprises: applying the lactase composition to a food article or using the lactase composition in the course of consuming the food article. The composition comprises a plurality of particles comprising lactase and a protective material, and the particles have a size that is not perceptible or barely perceptible on the human tongue. Embodiments of the particulate composition are as described above. The food article can be any dairy product.

The composition described herein can be applied to or otherwise included in any food article that includes lactose. The microencapsulated lactase beads are too small to be perceived by the human tongue, and the beads or particles are tasteless. These particles or beads are essentially imperceptible during digestion.

An average serving of each food embedded with lactase beads can have at least the equivalent activity of two typical (9000 units) lactase tablets.

The formulation can be included in any food articles that include lactose. Some examples of food articles include ice cream products, milk supplements, smoothies, specialty coffees, pizza and pasta. Some exemplary ice cream items that can include the formulation described herein include, e.g., chocolate syrups, marshmallow syrups, sprinkles—all flavors and including both standard and crunch types—mix-ins such as pieces of cookies, candy bars, raisins, chocolate chips and other such products typically offered in commercial ice cream parlors. Some exemplary milk supplement items that can include the formulation described herein include, e.g., chocolate milk syrups and powders. Some examples of smoothies items that can include the formulation described herein include, e.g., protein additives. Some examples of specialty coffee items that can include the formulation described herein include, e.g., caramel additives, cinnamon additives, cocoa and chocolate additives. Some examples of pizza and pasta items that can include the formulation described herein include, e.g., pizza toppings, and parmesan and romano cheese toppings.

In some embodiments, the products to embed the formulation described herein can be chocolate syrup or sprinkles. The formulation can be served with ice cream. For example, the formulation can be included in ice cream products sold in ice cream parlors and grocery stores for home use.

In some embodiments, the formulation described herein can be included in products such as marshmallow and caramel toppings.

In some embodiments, the formulation described herein can be included in a coffee product. The coffee product can be any coffee products that include lactose. For example, such coffee products include cappuccinos, lattes, chais and other milk-containing drinks served at coffee shops. The formulation can be included in any condiments found at coffee shops, such as cinnamon and powdered cocoa. In some embodiments, the formulation can be formulated in an imperceptible liquid or powder form such that it can be added by a barista when preparing a whipped coffee drink.

Some other food articles that can include the formulation described herein include food additives for smoothies, cream sauces at restaurants, yogurts and cheeses.

In some embodiments, the formulation described herein can be formulated into a thin-strip article that includes lactase. Thin strips are flat dissolvable delivery mechanisms. The benefits of this vehicle over the current tablet format are that they are easier for people without purses to carry (such as in a wallet), and they are easier for children to ingest in settings where no food-based preparation is available.

EXAMPLES

Lactase Formulations

Summary

Processes and formulations were designed to improve the stability of lactase in various food preparations. Portions of lactase were coated in a fluidized bed and granulated in a high shear granulator using two different polymeric systems for each process; shellac/HPMC and gum acacia gum/HPMC. Three food preparations were chosen for lactase addition; ice cream, coffee latte, and hot fudge. The moisture, temperature and pH were recorded for each sample initially and after two weeks. An assay method for testing processed lactase was developed and samples of each food preparation were assayed initially and after two weeks to determine lactase stability. In addition, unprocessed lactase activity was measured at various pH's to determine the range at which lactase is most active.

Experimental

Materials

The materials used in the studies herein and the makers thereof are summarized below.

| Ingredient | Lot # | Manufacturer |
|---|---|---|
| Hot fudge (18 oz) | NA | Smuckers |
| Coffee latte (16 oz) | NA | Starbucks |
| Vanilla Ice Cream | NA | Emerson |
| Lactase | 70229307 | National Enzyme Company |
| Hydroxypropyl Methylcellulose (HPMC) | 6076437 | Shinetzu |
| Triacetin | 530364197 | Univar |
| Marcoat (Shellac System, 25% Solids) | M070401 | Emerson Resources |
| Gum *Acacia* | K85904J15 | Ruger Chem. Co. |
| Glycerin | MV096824160 | Proctor & Gamble |

Testing pH—The pH was measured using an Orion probe submerged in the media until a stabilized reading was achieved.

LOD—Loss on drying was measured by placing an approximate 1 g sample in the moisture analyzer using test 50° C. A90.

Assay—The lactase was assayed using test method #C20229 provided by the National Enzyme Company. The specifications and validated compendial methods of Acid Lactase Units (ALU) are employed per the Food Chemical Codex fourth edition (FCC IV).

Overview

Two polymeric systems and two manufacturing processes were chosen as means to improve the stability of lactase in various food preparations. The shellac/HPMC system was chosen for its ability to protect against moisture, form an oxygen barrier, and for its enteric tendencies. Shellac systems are commonly used in food preparations as confectioner's glaze. The gum acacia/HPMC system was also chosen for its protective qualities, creating a less permeable barrier to protect the lactase in the stomach against acidic pH's. Two methods for applying these polymeric systems were selected. Fluidized bed coating was selected as a means to apply a thin layer evenly over each individual lactase particle. High shear granulation was used to agglomerate lactase particles in order to form granules.

In a previous study (data not shown), three food types were chosen based on pH and temperature; ice cream, hot fudge, and a coffee latte. In order to compare the results determined in this study with those in the previous study, the same three foods were selected. Each was purchased or prepared according to directions and 9000 lactase units per serving size were added. At the time of addition, the food samples were tested for pH and temperature. Immediately following, the samples were assayed for lactase activity. The samples were maintained for two weeks following testing in appropriate storage conditions and retested for lactase activity following the two week period.

Formulation A. Shellac/HPMC Granulation, Lot #CW12-125

The shellac/HPMC granulation was prepared using the following formulation and processing method:

| Ingredient | % solids | % w/w | g/batch | $g_{solids}$/batch |
|---|---|---|---|---|
| HPMC | 100.0% | 6.0% | 21.00 | 21.00 |
| Triacetin | 100.0% | 2.0% | 7.00 | 7.00 |
| Marcoat | 25.0% | 48.0% | 168.00 | 42.00 |
| DI Water | 0.0% | 44.0% | 154.00 | 0.00 |
| Total | 20.0% | 100.0% | 350.00 | 70.00 |
| Lactase | 100.0% | 100.0% | 300.00 | 300.00 |

Procedure:
 a) Begin mixing DI water w/vortex. Add the marcoat and triacetin to the mixing water.
 b) Slowly add the HPMC to (1). Continue to mix w/vortex for approximately 1 hour.
 c) Allow solution to deaerate prior to granulating.
 d) Add 300 g lactase to the 1 L granulator bowl. Begin mixing with the mixing blade set at 1350 rpm and chopper blade set at 3600 rpm.
 e) Slowly add the solution to the granular until lactase is adequately granulated. Record the amount of solution added.

Solution was added drop-wise to the granular until 70.1 g had been added. Thus, 14.02 g of solids were added, resulting in a theoretical weight gain of 4.67%. Therefore, 9000 lactase units would be equivalent to 94 mg of granulation. Once granulated, the material was collected and placed on a stainless steel tray in an oven set at 35° C. for approximately 18 hours in order to expedite drying.

Formulation B. Gum Acacia/HPMC Granulation, Lot #CW12-127

The gum acacia/HPMC granulation was prepared using the following formulation and processing method:

| Ingredient | % solids | % w/w | g/batch | $g_{solids}$/batch |
|---|---|---|---|---|
| *Acacia* | 100.0% | 9.0% | 27.00 | 27.00 |
| HPMC | 100.0% | 9.0% | 27.00 | 27.00 |
| Glycerin | 100.0% | 2.0% | 6.00 | 6.00 |
| DI Water | 0.0% | 80.0% | 240.00 | 0.00 |
| Total | 20.0% | 100.0% | 300.00 | 60.00 |
| Lactase | 100.0% | 100.0% | 300.00 | 300.00 |

Procedure:

a) Begin mixing DI water w/vortex. Add the glycerin to the mixing water.
b) Bag blend the HPMC and Acacia.
c) Slowly add (2) to (1). Continue to mix w/vortex for approx. 1 hour.
d) Allow solution to deaerate prior to granulating.
e) Add 300 g lactase to the 1 L granulator bowl. Begin mixing with the mixing blade set at 1350 pm and chopper blade set at 3600 rpm.
f) Slowly add the solution to the granulator until lactase is adequately granulated. Record the amount of solution added.

Solution was added dropwise until 70.2 g of solution had been added, resulting in a theoretical weight gain of 4.68%. Again, 94 mg of granulation would be the equivalence of 9000 lactase units. The granulation was placed in the same 35° C. oven and dried for approximately 18 hours.

Formulation C. Shellac/HPMC Coating, Lot #CW12-128

The shellac/HPMC granulation was prepared using the following formulation and processing method:

| Ingredient | % solids | % w/w | g/batch | $g_{solids}$/batch |
|---|---|---|---|---|
| HPMC | 100.0% | 4.5% | 54.00 | 54.00 |
| Triacetin | 100.0% | 1.5% | 18.00 | 18.00 |
| Marcoat | 25.0% | 36.0% | 432.00 | 108.00 |
| DI Water | 0.0% | 58.0% | 696.00 | 0.00 |
| Total | 15.0% | 100.0% | 1200.00 | 180.00 |
| Lactase | 100.0% | 100.0% | 650.00 | 650.00 |

Procedure:

a) Begin mixing DI water w/vortex. Add the marcoat and triacetin to the mixing water.
b) Slowly add the HPMC to (1). Continue to mix w/vortex for approx. 1 hour.
c) Allow solution to deaerate prior to coating. Use the coating parameters as guidelines.

Coating Parameters:

| | | | |
|---|---|---|---|
| Product Temp: | 47-48° C. | Spray Rate: | 15-22 g/min |
| Air Flow: | 50 cfu | Liquid Nozzle: | 1.0 mm |
| Atomization Air: | 30 psi | | |
| Inlet Temp: | 75-80° C. | Air Cap: | 2.0 mm |

Once the solution preparation was completed, 650 g of lactase were added to the vector FLM-1 fluid bed. The lactase was fluidized and heated. Spraying of the solution began once the product temperature was adequate. A weight gain of 20% was desired and solution was sprayed until the theoretical amount had been applied, assuming 90% coating efficiency. Thus, 108 mg of coated lactase would be equivalent to 9000 lactase units.

Actual coating parameters were recorded and are as follows in Table 1.

TABLE 1

Coating parameters used during manufacturing of lot CW12-128.

| Time (min) | Mass Sprayed (g) | Spray Rate (g/min) | Inlet Temp. (° C.) | Product Temp. (° C.) | Air Flow (cfm) | Nozzle Air (psi) |
|---|---|---|---|---|---|---|
| 0 | 0.0 | — | 85.6 | 45.8 | 19 | — |
| 4 | 65.0 | 16.3 | 86.0 | 38.7 | 28 | 30 |
| 8 | 124.9 | 15.0 | 90.9 | 38.2 | 32 | 30 |
| 13 | 198.9 | 14.8 | 89.8 | 39.0 | 32 | 30 |
| 21 | 317.8 | 14.9 | 90.4 | 41.3 | 33 | 30 |
| 29 | 438.7 | 15.1 | 90.7 | 42.1 | 34 | 30 |
| 38 | 572.4 | 14.9 | 91.1 | 42.8 | 34 | 30 |
| 49 | 737.2 | 15.0 | 89.4 | 44.2 | 33 | 30 |
| 57 | 857.2 | 15.0 | 89.9 | 44.4 | 33 | 30 |
| 64 | 963.1 | 15.1 | 89.8 | 44.5 | 32 | 30 |

Despite the lower than desired product temperature, the coating process performed well with no processing issues observed. It is likely that despite increasing the inlet temperature, the lower air flow volume resulted in the cooler temperatures. The air flow rate was only increased to 30 cfu as this amount was adequate to fluidize the bed.

Formulation D. Gum Acacia/Coating, Lot #CW12-129

The gum acacia/HPMC granulation was prepared using the following formulation and processing method:

| Ingredient | % solids | % w/w | g/batch | $g_{solids}$/batch |
|---|---|---|---|---|
| Acacia | 100.0% | 6.8% | 81.00 | 81.00 |
| HPMC | 100.0% | 6.8% | 81.00 | 81.00 |
| Glycerin | 100.0% | 1.5% | 18.00 | 18.00 |
| DI Water | 0.0% | 85.0% | 1020.00 | 0.00 |
| Total | 15.0% | 100.0% | 1200.00 | 180.00 |
| Lactase | 100.0% | 100.0% | 650.00 | 650.00 |

Procedure:

a) Mix the glycerol and DI water until mixed with vortex.
b) Bag blend the acacia and HPMC.
c) Add (b) to (a) and continue to mix with vortex for approximately 1 hour.
d) Allow solution to deaerate prior to spray coating. Use the coating parameters as guidelines.

Coating Parameters:

| Product Temp: | 47-48° C. | Spray Rate: | 15-22 g/min |
|---|---|---|---|
| Air Flow: | 50 cfu | Liquid Nozzle: | 1.0 mm |
| Atomization Air: | 30 psi | | |
| Inlet Temp: | 75-80° C. | Air Cap: | 2.0 mm |

The acacia gum coating system was prepared in the same manner described for the previous coating trial. A theoretical weight gain of 20% was again targeted and is assumed that 108 mg coated lactase is equivalent to 9000 lactase units.

The coating parameters were recorded and are as follows in Table 2.

TABLE 2

Coating parameters used during manufacturing of lot CW12-129.

| Time (min) | Mass Sprayed (g) | Spray Rate (g/min) | Inlet Temp. (° C.) | Product Temp. (° C.) | Air flow (cfm) | Nozzle Air (psi) |
|---|---|---|---|---|---|---|
| 0 | 0.0 | — | — | — | — | — |
| 2 | 31.5 | 15.8 | 89.9 | 41.5 | 26 | 30 |
| 12 | 185.5 | 15.4 | 91.2 | 40.0 | 29 | 30 |
| 20 | 304.7 | 14.9 | 90.0 | 40.4 | 30 | 30 |
| 27 | 411.4 | 15.2 | 90.6 | 41.3 | 30 | 30 |
| 37 | 569.3 | 15.8 | 91.0 | 41.7 | 30 | 30 |
| 44 | 681.7 | 16.1 | 90.7 | 41.9 | 30 | 30 |
| 54 | 844.2 | 16.3 | 89.5 | 41.9 | 30 | 30 |
| 61 | 963.2 | 17.0 | 89.4 | 41.8 | 30 | 30 |

Again, a lower product temperature was observed, however, coating proceeded without concern.

Ice Cream

Vanilla ice cream was prepared using the following recipe:

1 cup whole milk,

¾ cup granulated sugar, 2 cups heavy cream, 1-2 teaspoons pure vanilla extract, 9000 units lactase per serving—(719.6 mg lactase, serving size approximately ½ cup ice cream).

The above ingredients were used to form ice cream with lactase according to the following procedures:

a. Whisk the milk and granulated sugar in a bowl until the sugar is dissolved, about 1-2 minutes.

b. Stir in the heavy cream and vanilla.

c. Turn the ice cream maker on and pour the mixture into the freezer bowl. Allow to thicken 20-25 min.

d. Continue to churn for 1-2 hours.

e. Keep frozen.

Once prepared, the ice cream was divided into 4 portions, each of which contained two servings. Additionally, portions of processed lactase were added to each so that the equivalence of the theoretical amount calculated to be 9000 lactase units was added to each serving.

TABLE 3

Mass of processed lactase added to each portion of ice cream.

| | Shellac Granulation, CW12-125 | *Acacia* Granulation, CW12-127 | Shellac Coating, CW12-128 | *Acacia* Coating, CW12-129 |
|---|---|---|---|---|
| Mass of Ice Cream (g) | 173.1 | 173.0 | 172.8 | 173.0 |
| Mass of Processed Lactase (mg) | 191 | 190 | 216 | 216 |

Hot Fudge

The hot fudge was prepared according to the package label. Portions were separated into 4 glass containers, each a single serving. Processed lactase, theoretically equivalent to 9000 lactase units, was then added to each, tested, and stored in an 80° oven (Table 4).

TABLE 4

Mass of processed lactase added to each portion of hot fudge.

| | Shellac Granulation, CW12-125 | *Acacia* Granulation, CW12-127 | Shellac Coating, CW12-128 | *Acacia* Coating, CW12-129 |
|---|---|---|---|---|
| Mass of Hot Fudge (g) | 38.9 | 39.0 | 39.0 | 39.0 |
| Mass of Processed Lactase (mg) | 95.1 | 95.6 | 110.7 | 110.2 |

Starbucks Coffee Latte, 16 oz

Four, 16 oz coffee lattes were purchased from Starbucks. The theoretical equivalence of 9000 lactase units was immediately added to each. The samples 9 table 5) were then transferred to glass jars and placed in an 80° C. oven for two week storage.

TABLE 5

Mass of processed lactase added to each portion of coffee latte.

| | Shellac Granulation, CW12-125 | *Acacia* Granulation, CW12-127 | Shellac Coating, CW12-128 | *Acacia* Coating, CW12-129 |
|---|---|---|---|---|
| Mass of coffee latte (g) | 472.0 | 485.8 | 471.0 | 109.4 |
| Mass of Processed Lactase (mg) | 95.1 | 95.2 | 108.6 | 109.4 |

Results and Discussion

Lactase Characterization

Unprocessed and processed lactase was characterized for moisture, density, and particle size. The results are shown in the tables below in Table 6.

TABLE 6

Bulk and tapped densities for unprocessed and processed lactase.
Density (g/ml)

| Sample | Mass (g) | Initial Volume (mL) | Final Volume (mL) | Bulk Density (g/mL) | Tapped Density (g/mL) |
|---|---|---|---|---|---|
| Shellac Granulation, Lot #CW12-125 | 67.9 | 100 | 86 | 0.68 | 0.79 |
| Acacia Granulation, Lot #CW12-127 | 64.1 | 100 | 83 | 0.64 | 0.77 |
| Shellac Coating, Lot #CW12-128 | 39.5 | 100 | 84 | 0.40 | 0.47 |
| Acacia Coating, Lot #CW12-129 | 37.5 | 100 | 81 | 0.38 | 0.46 |
| Lactase, Lot #70229307 | 53 | 100 | 80 | 0.53 | 0.66 |

TABLE 7

Moisture content for lactase, processed lactase, and three food types*.
Initial Moisture Content (50° C., A90)

| Sample | Initial Weight (g) | % Moisture |
|---|---|---|
| Shellac Granulation, Lot #CW12-125 | 0.995 | 98.99 |
| Acacia Granulation, Lot #CW12-127 | 1.002 | 99.20 |
| Shellac Coating, Lot #CW12-128 | 1.004 | 99.00 |
| Acacia Coating, Lot #CW12-129 | 1.001 | 97.40 |
| Ice Cream (time zero) | 1.020 | 45.20 |
| Hot Fudge (time zero) | 1.019 | 94.79 |
| Latte (time zero) | 1.024 | 10.74 |
| Lactase, Lot #70229307 | 1.000 | 99.40 |

*The test was run at 50° C. and was complete once the rate of weight loss was less than 1 mg/90 sec.

Figure 1:
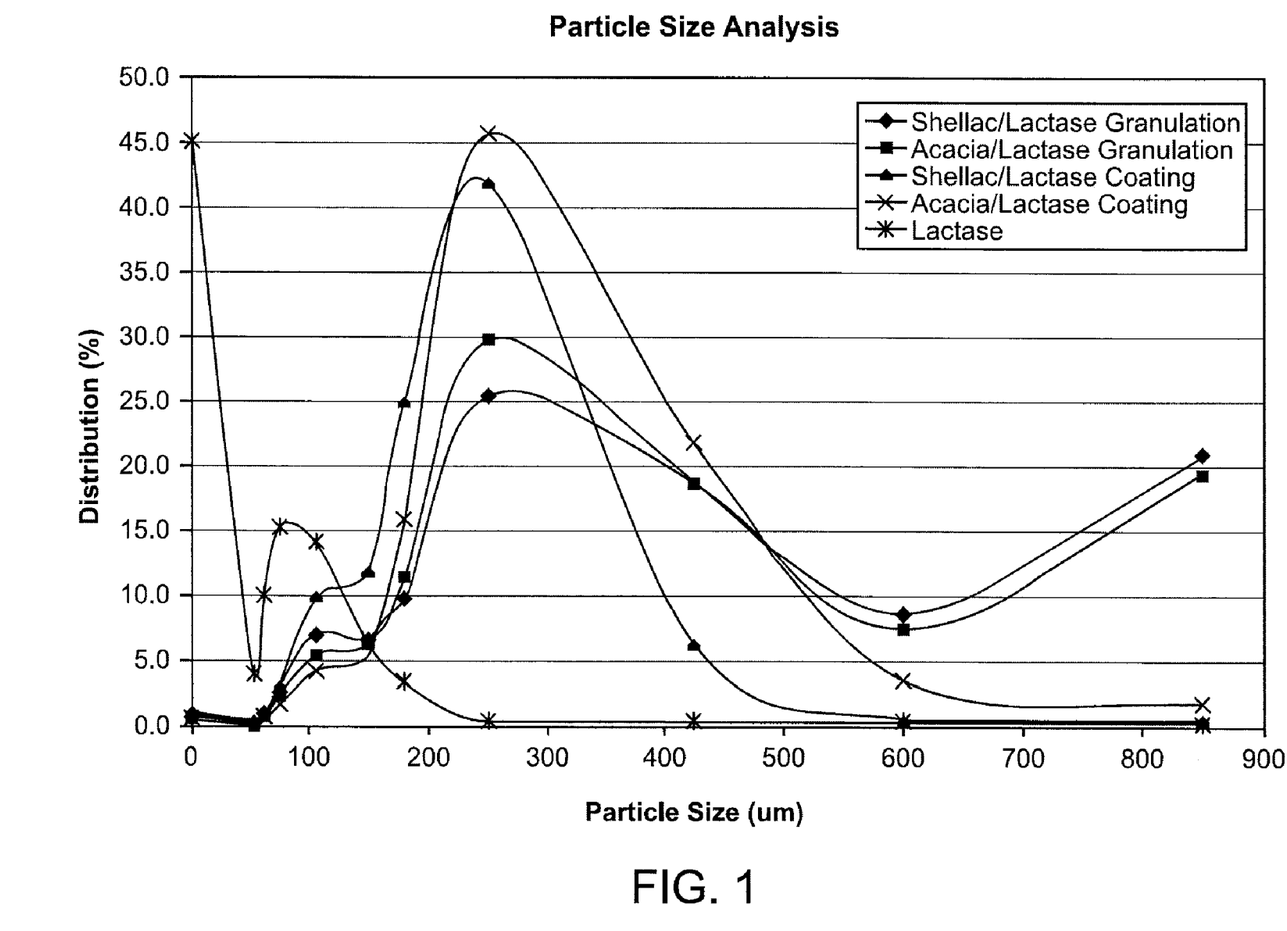
FIG. 1. Particle size distribution for four lots of processed lactase.

The particle size distribution for four lots of processed lactase is shown in FIG. 1. Average particle size for the four lots of processed lactase is summarized in Table 8, below.

TABLE 8

Average particle size for four lots of processed lactase.

| Sample | Average Particle Size (μm) |
|---|---|
| Shellac Granulation, Lot #CW12-125 | 396.6 |
| Acacia Granulation, Lot #CW12-127 | 387.6 |
| Shellac Coating, Lot #CW12-128 | 243.3 |
| Acacia Coating, Lot #CW12-129 | 319.6 |

The particle size data indicated that, as expected, the granulated particles were much larger than their coated counterparts. As a result, the granulated lactase was visible in both the ice cream and hot fudge after addition.

Food Characterization

TABLE 9 pH measurements for processed lactase/food samples measured initially and after two weeks.

pH Measurements of Lactase Treated Foods

| | Ice Cream | | | | Hot Fudge | | | | Coffee Latte | | | |
|---|---|---|---|---|---|---|---|---|---|---|---|---|
| | SC | SG | AC | AG | SC | SG | AC | AG | SC | SG | AC | AG |
| Initial | 6.05 | 6.29 | 6.51 | 6.55 | 6.00 | 5.91 | 5.97 | 5.88 | 6.50 | 6.46 | 6.47 | 6.50 |
| Final | 6.40 | 6.34 | 6.36 | 6.43 | 4.19 | 3.86 | 3.97 | 4.04 | 4.89 | 4.94 | 4.89 | 5.04 |

TABLE 10

Temperature of food media at time of processed lactase addition.
Temperature at Addition (° C.)

| Ice Cream | −4 |
|---|---|
| Hot Fudge | 48 |
| Coffee Latte | 63 |

Lactase Activity

Processed lactase activity was measured over a range of pH's to determine the optimal environment for activity. Seven buffer solutions, from pH 1 to pH 7, were prepared. Processed lactase was added to each and the activity was measured. The pH of the lactase/pH 1 solution was then raised to pH 7. The activity was again measured to determine whether certain pH's damage the enzyme or just deactivate it. The activity data is shown in the tables and chart below.

TABLE 11

Acacia coated lactase activity over a pH range of 1 to 7.

Acacia Coated Lactase, % Recovered

| Replicate | pH 1 | pH 2 | pH 3 | pH 4 | pH 5 | pH 6 | pH 7 | pH 1 raised to 7 |
|---|---|---|---|---|---|---|---|---|
| 1 | 7.1% | −0.3% | 2.4% | 66.4% | 66.1% | 65.4% | 91.7% | 66.6% |
| 2 | 0.5% | −0.4% | 6.3% | 97.5% | 107.1% | 86.8% | 81.6% | 105.6% |
| 3 | 1.3% | 0.1% | 5.2% | 67.3% | 89.6% | 80.0% | 91.6% | 86.5% |
| Average | 3.0% | −0.2% | 4.6% | 77.1% | 87.6% | 77.4% | 88.3% | 86.2% |
| Std. Dev. | 3.6% | 0.2% | 2.0% | 17.7% | 20.6% | 10.9% | 5.8% | 19.5% |

TABLE 12

Acacia granulated lactase activity over a pH range of 1 to 7.

Acacia Granulated Lactase, % Recovered

| Replicate | pH 1 | pH 2 | pH 3 | pH 4 | pH 5 | pH 6 | pH 7 | pH 1 raised to 7 |
|---|---|---|---|---|---|---|---|---|
| 1 | 0.3% | 0.3% | 0.9% | 43.3% | 39.2% | 32.1% | 30.4% | −5.2% |
| 2 | 0.2% | 0.1% | 1.2% | 40.6% | 35.2% | 36.4% | 21.3% | 10.2% |
| 3 | 0.2% | 0.1% | 1.0% | 36.4% | 29.9% | 29.3% | 36.9% | −3.7% |
| Average | 0.2% | 0.2% | 1.0% | 40.1% | 34.8% | 32.6% | 29.5% | 0.4% |
| Std. Dev. | 0.0% | 0.2% | 0.2% | 3.5% | 4.6% | 3.6% | 7.8% | 8.5% |

TABLE 13

Shellac coated lactase activity over a pH range of 1 to 7.

Shellac Coated Lactase, % Recovered

| Replicate | pH 1 | pH 2 | pH 3 | pH 4 | pH 5 | pH 6 | pH 7 | pH 1 raised to 7 |
|---|---|---|---|---|---|---|---|---|
| 1 | 0.03% | 0.50% | 1.08% | 33.88% | 82.12% | 73.77% | 75.94% | 7.06% |
| 2 | −0.17% | 0.55% | 5.25% | 48.66% | 68.39% | 70.20% | 68.02% | 28.45% |
| 3 | −0.02% | 0.54% | 1.86% | 55.97% | 58.79% | 62.50% | 71.47% | 54.28% |
| Average | −0.1% | 0.5% | 2.7% | 46.2% | 69.8% | 68.8% | 71.8% | 29.9% |
| Std. Dev. | 0.1% | 0.0% | 2.2% | 11.3% | 11.7% | 5.8% | 4.0% | 23.6% |

TABLE 14

Shellac granulated lactase activity over a pH range of 1 to 7.

Shellac Granulated Lactase, % Recovered

| Replicate | pH 1 | pH 2 | pH 3 | pH 4 | pH 5 | pH 6 | pH 7 | pH 1 raised to 7 |
|---|---|---|---|---|---|---|---|---|
| 1 | 1.7% | 0.5% | 0.8% | 71.7% | 70.4% | 79.8% | 61.3% | 5.5% |
| 2 | −0.6% | 0.5% | 1.2% | 58.8% | 90.5% | 64.6% | 67.8% | 5.0% |
| 3 | −0.9% | 0.7% | 3.7% | 56.2% | 65.1% | 44.3% | 50.5% | 0.6% |
| Average | 0.1% | 0.6% | 1.9% | 62.2% | 75.3% | 62.9% | 59.8% | 3.7% |
| Std. Dev. | 1.4% | 0.1% | 1.6% | 8.3% | 13.4% | 17.8% | 8.7% | 2.7% |

Figure 2:
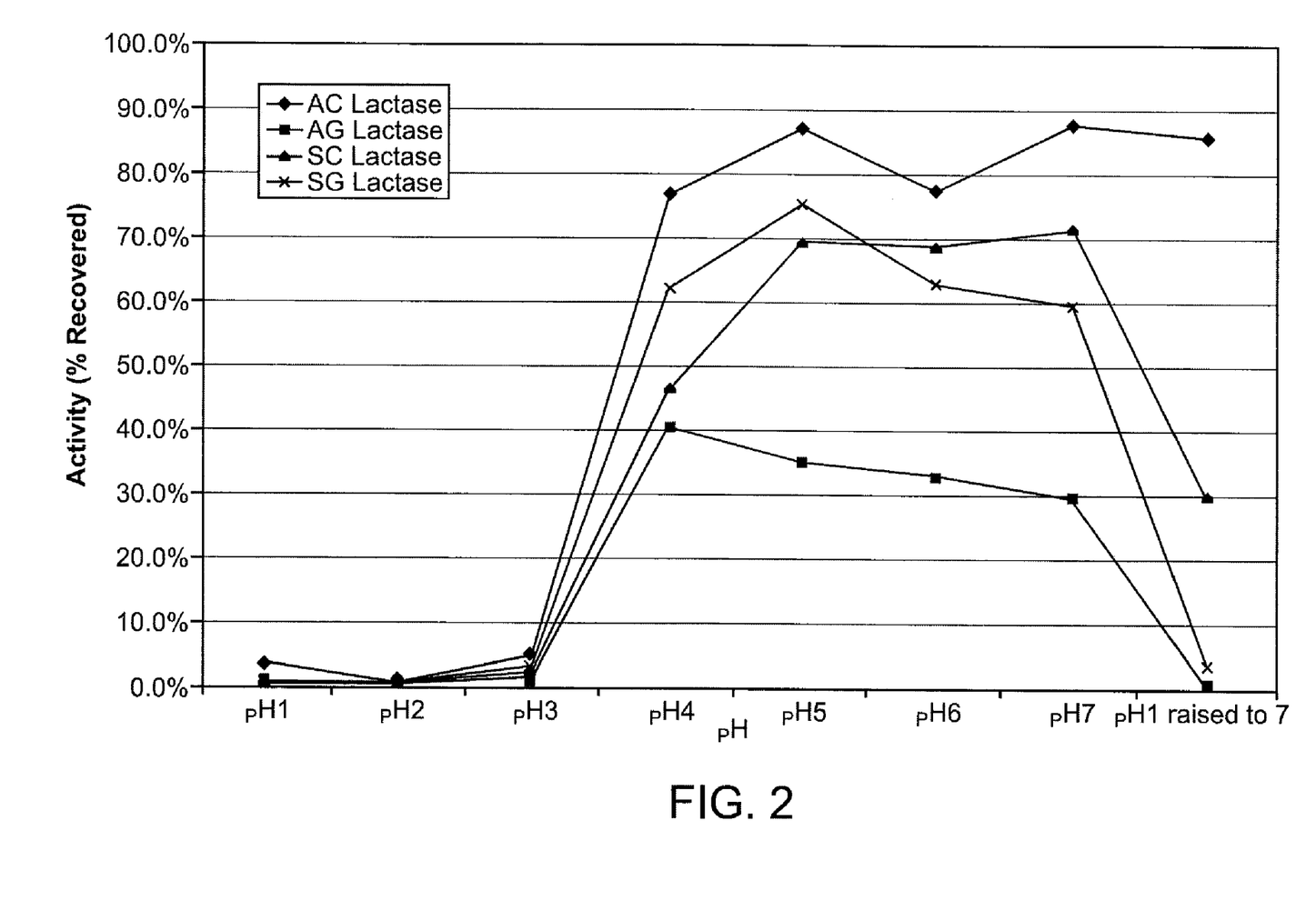
FIG. 2. Lactase activity measured for four lots of processed lactase lots; acacia coated lactase (AC) lot #CW12-29, acacia granulated lactase (AG) lot #CW12-127, shellac coated lactase (SC) lot #CW12-128, and shellac granulated lactase (SG) lot #CW12-125.

Lactase activity profiles for four lots of processed lactase are shown in FIG. 2: acacia coated lactase (AC) lot #CW12-29, acacia granulated lactase (AG) lot #CW12-127, shellac coated lactase (SC) lot #CW12-128, and shellac granulated lactase (SG) lot #CW12-125. The lactase activity profiles show that lactase is most active at pH's between 5 and 7. It also shows inactivity at pH 3 and below. The samples prepared at pH 1 and raised to pH 7, however, show an increase of activity. This indicates one of two things; that the lactase is inactive in highly acidic pH's but becomes active in more basic environments or that the acacia and shellac protect the lactase in acidic conditions but release the lactase once in a neutral environment. The higher activities in both the shellac and acacia coated lactase, as opposed to the granulated lactase, support the latter hypothesis, suggesting that the coating process protects the enzyme.

In addition to the pH profile, lactase activity was also measured for each of the four processed lactase types added to three foods; ice cream, coffee latte, and hot fudge.

Activity was measured initially at the time of sample preparation and again after two weeks storage. Results for each food type are shown below.

TABLE 15

Processed lactase activity in ice cream.

Lactase Activity in Ice Cream (% Recovered)

| | | Shellac Granulation, Lot #CW12-125 | *Acacia* Granulation, Lot #CW12-127 | Shellac Coating, Lot #CW12-128 | *Acacia* Coating, Lot #CW12-129 |
|---|---|---|---|---|---|
| Initial (Time Zero) | 1 | 109.3% | 76.9% | 111.90% | 70.8% |
| | 2 | 115.9% | 76.5% | 118.61% | 63.6% |
| | 3 | 114.0% | 73.4% | 116.69% | 68.5% |
| | Average | 113.17% | 75.6% | 115.7% | 67.67% |
| | Std. Dev. | 3.4% | 1.9% | 3.5% | 3.7% |
| Final (Two Week) | 1 | 101.49% | 95.06% | 66.92% | 79.45% |
| | 2 | 123.67% | 98.72% | 163.99% | 98.12% |
| | 3 | 57.30% | 102.19% | 74.68% | 94.07% |
| | Average | 94.2% | 98.7% | 101.9% | 90.5% |
| | Std. Dev. | 33.8% | 3.6% | 53.9% | 9.8% |

TABLE 16

Processed lactase activity in coffee.

Lactase Activity in Coffee Latte (% Recovered)

| | | Shellac Granulation, Lot #CW12-125 | *Acacia* Granulation, Lot #CW12-127 | Shellac Coating, Lot #CW12-128 | *Acacia* Coating, Lot #CW12-129 |
|---|---|---|---|---|---|
| Initial (Time Zero) | 1 | −7.0% | 8.2% | −13.1% | −4.4% |
| | 2 | −10.2% | −13.3% | −3.6% | −4.7% |
| | 3 | −11.6% | −11.4% | −5.8% | −3.4% |
| | Average | −9.6% | −5.5% | −7.5% | −4.2% |
| | Std. Dev. | 2.4% | 11.9% | 5.0% | 0.6% |
| Final (Two Week) | 1 | 4.4% | 47.4% | 13.0% | 12.2% |
| | 2 | 24.4% | 65.9% | 11.5% | 12.8% |
| | 3 | 54.8% | 30.9% | 13.7% | 26.1% |
| | Average | 27.9% | 48.1% | 12.8% | 17.0% |
| | Std. Dev. | 25.4% | 17.5% | 1.1% | 7.8% |

TABLE 17

Processed lactase activity in hot fudge.

Lactase Activity in Hot Fudge (% Recovered)

| | | Shellac Granulation, Lot #CW12-125 | *Acacia* Granulation, Lot #CW12-127 | Shellac Coating, Lot #CW12-128 | *Acacia* Coating, Lot #CW12-129 |
|---|---|---|---|---|---|
| Initial (Time Zero) | 1 | 35.5% | 11.7% | 4.24% | 51.5% |
| | 2 | 31.4% | 12.7% | −5.75% | 51.6% |
| | 3 | 8.6% | 12.8% | −5.07% | 57.9% |
| | Average | 25.15% | 12.38% | −2.19% | 53.69% |
| | Std. Dev. | 14.48% | 0.63% | 5.59% | 3.66% |
| Final (Two Week) | 1 | −6.38% | 7.95% | 5.21% | 6.97% |
| | 2 | −0.30% | 41.04% | 6.49% | −2.08% |
| | 3 | −1.29% | 13.89% | 2.92% | −4.73% |
| | Average | −2.65% | 20.96% | 4.87% | 0.05% |
| | Std. Dev. | 3.26% | 17.64% | 1.81% | 6.14% |

The activities measured for each processed lactase added to ice cream indicate that, similar to the results seen in the previous study performed at Emerson, the near neutral pH and cold storage conditions of the ice cream preserve lactase activity. The increase of activity seen in the acacia processed lactases indicate initial protection of the enzyme at time zero with a degradation of the barrier over the two week period, releasing the enzyme in full. The shellac barrier, on the other hand, appears to release immediately after addition and thus leave the lactase unprotected for the full two weeks, resulting in a slight decrease of activity.

The processed lactase activities measured for the coffee latte samples each increase over the two week period. Initially, each lot shows no measurable activity. The high temperature in conjunction with the protective barriers could prohibit activity and therefore be the result of lactase inactivity. After the two week storage period, each lot shows low levels of lactase activity, with the acacia processed lactase again proving more stable. Despite the continually high temperature and slightly acidic environment, it appears that the coatings continue to protect over a lengthened time period.

Finally, lactase activities measured for each processed lot added to hot fudge indicate the barriers do not protect over the two week period. It is assumed that the high temperatures and decreasing pH result in the inactivity of the lactase.

Conclusion

Similar to the results seen in the previous study, it is proven that the activity of lactase, treated or untreated, is more stable in cold, neutral environments. Again, lactase activity is limited in acidic or high temperature environments. It does appear, however, that both shellac and acacia provide some protection, seen by both the increase of activity in the pH profile of the 1 to 7 pH samples and by the activity increase seen after two weeks in the coffee latte sample. It also appears that of the two polymers, acacia provides a better protection.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of using a solid lactase composition in particulate form to treat lactose intolerance upon ingestion of a food article comprising lactose, the lactase composition consisting essentially of a plurality of particles, wherein the particles consist essentially of a lactase in solid form and a protective material as a matrix material with the lactase dispersed within the protective material, configured such that the protective material stabilizes the lactase in the food article from the lactose prior to ingestion and wherein the protective material dissolves in acidic or basic environment to release the lactase with the food article upon consumption of the food article such that the lactase and the particles are in the presence of the food article during release of the lactase from the particles for the lactase to hydrolyze the lactose from the food article, the method comprising applying the lactase composition in particulate form to the food article or using the lactase composition in the course of consuming the food article, wherein the particles have a size that is not perceptible or barely perceptible on the human tongue such that upon consuming the food article the composition in particulate form is not perceptible or is barely perceptible on the human tongue; and wherein the lactase composition is in the form of a powder or a powder within a thin strip.

2. The method of claim 1, wherein the particles have a size of about 400 microns or below.

3. The method of claim 1, wherein the particles have a size of about 200 microns or below.

4. The method of claim 1, wherein the particles have a size of about 100 microns or below.

5. The method of claim 1, wherein the particles have a size of about 50 microns or below.

6. The method of claim 1, wherein the particles are microcapsules encapsulating lactase.

7. The method of claim 1, wherein the protective material forms a coating around the lactase.

8. The method of claim 1, wherein the lactase has a concentration from about 5 wt % to about 95 wt % by total weight of the formulation.

9. The method of claim 1, wherein the protective material is selected from the group consisting of amylose acetate phthalates, styrene-maleic acid copolymer, cellulose acetate succinate, cellulose acetate phthalate, polyvinyl acetate phthalate, hydroxypropylmethylcellulose phthalate, fatty acids, hydroxypropyl methylcellulose (HPMC), glycerol triacetate (triacetin), Marcoat, gum acacia, glycerin, fatty acid esters, glycerol esters, polyglycerol esters, paraffin waxes, carnauba wax, formalized gelatin, shellac wax, hydrogenated vegetable waxes, and combinations thereof.

10. The method of claim 1, wherein the food article is a dairy product.

11. The method of claim 1, wherein the food article is selected from milk, coffee, chocolate, cereals, smoothies, pizza, and ice cream.

12. The method of claim 1, wherein the lactase composition is configured to release lactase into the food once the food has passed the taste buds.

13. The method of claim 1, wherein the lactase composition releases lactase in acidic environment.

14. The method of claim 1, wherein the lactase composition releases lactase in basic environment.

15. The method of claim 1, wherein the lactase composition comprises a solid formulation.

16. The method of claim 15, wherein the solid lactase formulation further comprises one or more fillers or carriers.

17. The method of claim 1, wherein the lactase composition comprises a liquid formulation.

18. The method of claim 17, wherein the liquid lactase formulation further comprises one or more suspending agents.

19. The method of claim 17, wherein the liquid lactase formulation comprises a suspension or dispersion of the lactase composition particles.

20. The method of claim 1 wherein the composition is formed from an aqueous solution of the protective material and lactase in solid form.

21. The method of claim 1, wherein the particles consist of the lactase in solid form and the protective material, whereby the protective material stabilizes the lactase in the food article from the lactose prior to ingestion.

22. The method of claim 1, wherein the plurality of particles are produced in a process that includes a step of filtering to provide particles of a size that is not perceptible on the human tongue.

23. The method of claim 1, wherein the lactase composition is in the form of a powder.

24. The method of claim 1, wherein the lactase composition is in the form of a powder within a thin strip.

* * * * *